United States Patent
Meinhold et al.

(10) Patent No.: US 9,360,589 B1
(45) Date of Patent: Jun. 7, 2016

(54) ARTICLES CONTAINING NON-VISIBLE IDENTIFYING MARKS FORMED FROM CARBON NANOMATERIALS AND METHODS UTILIZING THE SAME

(71) Applicant: LOCKHEED MARTIN CORPORATION, Bethesda, MD (US)

(72) Inventors: Mitchell W. Meinhold, Medford, MA (US); Jonathan W. Ward, San Jose, CA (US); Michael J. O'Connor, Manassas Park, VA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 14/537,830

(22) Filed: Nov. 10, 2014

Related U.S. Application Data

(63) Continuation-in-part of application No. 14/256,840, filed on Apr. 18, 2014, now Pat. No. 9,179,542.

(60) Provisional application No. 61/815,232, filed on Apr. 23, 2013.

(51) Int. Cl.
  *G01N 21/64* (2006.01)
  *G01V 15/00* (2006.01)
  (Continued)

(52) U.S. Cl.
  CPC ............... *G01V 15/00* (2013.01); *B82Y 15/00* (2013.01); *G06K 19/00* (2013.01); *G06K 19/077* (2013.01); *G06K 19/14* (2013.01); *B82Y 30/00* (2013.01); *Y10S 977/932* (2013.01)

(58) Field of Classification Search
  CPC ............................ G06K 19/06009; G06K 7/10
  USPC ........................................................ 250/459.1
  See application file for complete search history.

(56) References Cited

U.S. PATENT DOCUMENTS 7,572,426 B2    8/2009  Strano et al.
7,821,079 B2 *  10/2010 Cho et al. ............... 257/379
(Continued)

FOREIGN PATENT DOCUMENTS

| CN | 103018231 A | 4/2013 |
| JP | 08211025 A * | 8/1996 |
| WO | WO 2013100794 A1 * | 7/2013 |

OTHER PUBLICATIONS

Beuneu, "Nucleation of single wall carbon nanotubes of various chiralities," Solid State Communications, 2012, pp. 1155-1159, vol. 152.

(Continued)

*Primary Examiner* — Kiho Kim
(74) *Attorney, Agent, or Firm* — McDermott Will and Emery LLP

(57) ABSTRACT

Identifying marks are often used for authentication and tracking purposes with various types of articles, but the marks themselves can sometimes be subject to replication or removal by an outside entity, such as a person or group having malicious intent. This can make it easier for an outside entity to produce a counterfeit article or to sell a stolen article. Carbon nanotubes and other carbon nanomaterials can be used to form identifying marks that are not visible to the naked eye, thereby making the marks more difficult for an outside entity to tamper with. Various articles can include an identifying mark that is localized and not visible to the naked eye, the identifying mark being electrically conductive and containing a carbon nanomaterial. By electrically interrogating the article, such as through spatially measuring eddy currents about the article, the marks can be located and authenticated.

20 Claims, 7 Drawing Sheets

(51) Int. Cl.
  *G06K 19/077* (2006.01)
  *G06K 19/00* (2006.01)
  *G06K 19/14* (2006.01)
  *B82Y 15/00* (2011.01)
  *B82Y 30/00* (2011.01)

(56) References Cited

U.S. PATENT DOCUMENTS

| | | | |
|---|---|---|---|
| 2004/0126820 A1* | 7/2004 | Chan et al. | 435/7.4 |
| 2005/0156318 A1 | 7/2005 | Douglas | |
| 2008/0276817 A1 | 11/2008 | Hinch et al. | |
| 2010/0059595 A1* | 3/2010 | Longfu | 235/488 |
| 2010/0061619 A1* | 3/2010 | Boegli | 382/141 |
| 2010/0209632 A1* | 8/2010 | Weisman et al. | 428/29 |
| 2014/0205083 A1* | 7/2014 | Pryakhin et al. | 380/28 |

OTHER PUBLICATIONS

Ortolani, et al., "Chirality dependent surface adjesion of single-walled carbon nanotubes on graphene surfaces," Carbon, 2010, pp. 3050-3056, vol. 48.

Bachilo, et al., "Structure-assigned optical spectra of single-walled carbon nanotubes," Science, 2002, pp. 2361-2366, vol. 298.

* cited by examiner

ARTICLES CONTAINING NON-VISIBLE IDENTIFYING MARKS FORMED FROM CARBON NANOMATERIALS AND METHODS UTILIZING THE SAME

CROSS-REFERENCE TO RELATED APPLICATIONS

This application is a continuation-in-part of U.S. patent application Ser. No. 14/256,840, filed Apr. 18, 2014, which claims the benefit of priority under 35 U.S.C. §119 from U.S. Provisional Patent Application 61/815,232, filed Apr. 23, 2013, each of which is incorporated herein by reference in its entirety.

STATEMENT REGARDING FEDERALLY SPONSORED RESEARCH OR DEVELOPMENT

Not applicable.

FIELD

The present disclosure generally relates to carbon nanomaterials, and, more specifically, to methods for tracking and authenticating articles using carbon nanomaterials based upon their electrical properties.

BACKGROUND

Millions of dollars are lost annually by manufacturers due to the theft or misdirection of shipments of consumer goods. An even greater problem for manufacturers in many industries is the growing prevalence of counterfeit reproductions of their products. Counterfeit products can be problematic for a manufacturer in terms of lost revenue. Low quality counterfeit products can also unfairly taint the reputation of a manufacturer in the public's eyes, particularly if the public is unaware that a counterfeiting problem exists.

Tampering of articles by an outside entity attempting to reverse-engineer or alter the articles represents a significant concern for manufacturers. As used herein, the terms "tamper," "tampering," and other grammatical equivalents thereof will refer to any unauthorized use, access, investigation or alteration of an article, whether malicious or not. A number of anti-tampering protocols are often put into place by manufacturers to restrict an outside entity's ability to determine the true operational principles of an article. Particularly in the electronics industry, tampering represents an ongoing challenge for manufacturers. Some anti-tampering protocols focus on masking the true operational principles of an article, thereby making it difficult for an outside entity to reverse-engineer the article and produce a counterfeit copy.

Tampering can also involve removing, altering or replicating an identifying mark that serves to verify the authenticity of an article. The terms "mark," "tag" and grammatical equivalents thereof may be used synonymously herein. Removing, altering or replicating an identifying mark can be problematic from standpoints of both theft and counterfeiting. A number of identifying marks have been routinely used for tagging various articles, including bar codes, RFIDs, and the like. However, these types of identifying marks are often readily visible to an outside entity. With enough diligence, they can frequently be copied by an outside entity for marking counterfeit articles in much the same way as an authentic article. Likewise, removal, alteration, or replacement of a visible identifying mark from an authentic article can make the article untrackable and subject to theft.

In view of the foregoing, there remains a need to develop identifying marks providing an enhanced level of security. The present disclosure satisfies the foregoing need and provides related advantages as well.

SUMMARY

In various embodiments, articles described herein can include an identifying mark that is localized and not visible to the naked eye. The identifying mark is electrically conductive and contains a carbon nanomaterial.

In various embodiments, methods described herein can include incorporating an identifying mark on or within an article in need of tracking; operationally deploying the article; and after operationally deploying the article, electrically interrogating the article to locate and assay the identifying mark. The identifying mark is localized, electrically conductive, and not visible to the naked eye, and contains a carbon nanomaterial.

The foregoing has outlined rather broadly the features of the present disclosure in order that the detailed description that follows can be better understood. Additional features and advantages of the disclosure will be described hereinafter. These and other advantages and features will become more apparent from the description below taken in conjunction with the drawings.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
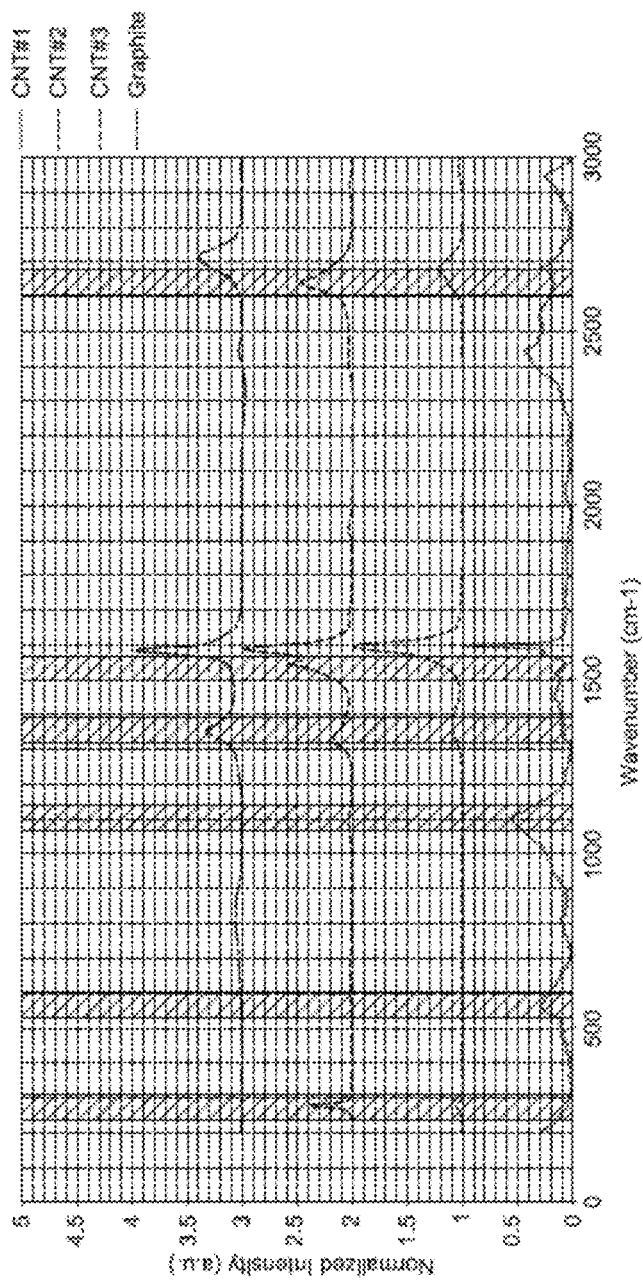
FIG. 1 shows a series of illustrative Raman spectra of various carbon nanotube samples that differ slightly in their chiral distribution.

The present disclosure is directed, in part, to articles containing an identifying mark formed from a carbon nanomaterial, the identifying mark being electrically conductive and not visible to the naked eye. The present disclosure is also directed, in part, to methods for tagging and authenticating various articles containing an identifying mark formed from a carbon nanomaterial, the identifying mark being electrically conductive and not visible to the naked eye.

Although applying or incorporating an identifying mark upon or within various articles can constitute a portion of a manufacturer's anti-tampering and security protocols, many types of marks are themselves subject to illicit copying or alteration, thereby defeating the purpose of the mark. In many instances, such marks are readily viewable by an outside entity with malicious intent, thereby providing an alert that the mark must also be replicated in producing a counterfeit article that is harder to identify as such. In the case of theft, a visible mark can alert an outside entity that the mark needs to be removed to prevent tracking of the stolen goods. Although identifying marks can be hidden from view or embedded within an article to preclude their observation by an outside entity, surveying the article through direct observation techniques to determine if the article is indeed marked can then become much more problematic. In some cases, it might even be necessary to damage the article to expose the mark, which can be particularly undesirable.

The present inventors discovered that carbon nanomaterials, particularly carbon nanotubes, graphene and/or functionalized variants thereof, optionally in combination with other types of carbonaceous materials, can be used in marking and tracking applications to provide significant advantages over conventionally used identifying marks. More specifically, the inventors discovered that the electrical properties of carbon nanomaterials, optionally in combination with the distinct spectroscopic properties of carbon nanotubes, could be leveraged to provide identifying marks with unique electrical and spectral signatures that are not easily replicable by an outside entity. Through proper utilization of these properties, identifying marks can be formed from carbon nanomaterials such that the marks are not visible to the naked eye, either by virtue of their small size or their location within an article. Effectively, such marks can be hidden within plain sight.

The electrical conductivity of carbon nanotubes and graphene is well known, and a number of applications have been proposed for incorporating these carbon nanomaterials within an article to enhance the article's electrical conductivity on the macroscale, such as through increasing the electrical conductivity of a matrix material above the carbon nanomaterial's electrical percolation threshold. In contrast to the traditional use of carbon nanomaterials for electrically enhancing articles on the macroscale, the present inventors recognized that electrically conductive carbon nanomaterials can be used for locally changing the electrical conductivity within a portion of an article, but without substantially enhancing the bulk electrical conductivity of the article itself. This feature can make carbon nanomaterials well suited for marking applications.

Although carbon nanomaterials can be electrically interrogated directly, for example by measuring the electrical conductivity across the carbon nanomaterials in a circuit, direct electrical interrogation is not especially suitable for marking applications for several reasons. Since identifying marks formed from carbon nanomaterials are intended to be difficult to view and locate, direct electrical conductivity measurements can be problematic to perform, even for a mark's owner with a general knowledge of the location and properties of the mark. Incorporating visible electrical leads in an article to facilitate direct electrical measurements of a mark can also provide general guidance as to the mark's location within the article, thereby defeating the "invisibility" advantage provided by the carbon nanomaterials. In addition to being technically problematic and revealing of a mark's location, direct electrical interrogation techniques can also be costly to implement.

In contrast to direct electrical interrogation techniques, the present inventors recognized that indirect electrical interrogation of an electrically conductive carbon nanomaterial can be particularly effective for marking applications. Indirect electrical interrogation techniques can be relatively simple to implement and can be accomplished in several different ways, as discussed further herein. In one configuration, eddy currents within an article can be assayed using an eddy current probe in order to locate an identifying mark and to determine if the mark has the correct electrical properties. In another configuration, electrically conductive identifying marks containing a carbon nanomaterial can be configured to be in resonant communication with one another. Thus, even if an outside entity is somehow able to discern that a carbon nanomaterial mark is present in an article, indirect electrical property measurements still provide additional security features over just the size and location of the mark. For example, in order to produce a true mark in a counterfeit article, the conductivity and resonant communication properties of the mark would also need to be replicated.

Indirect electrical interrogation of a mark, such as through eddy current measurement or resonant communication observation, can be complementary to spectroscopic assay techniques. Foremost, indirect electrical interrogation techniques can take place on an identifying mark that is disposed on the surface of the article or is buried within the article. In eddy current measurements, for example, the intervening material between the identifying mark and the eddy current probe is not particularly limited, provided that the intervening material is not substantially conductive. Thus, the inventors recognized that eddy current probe measurements can be effectively used for determining the location and conductivity of both surface and buried identifying marks within an article. In contrast, when assaying an identifying mark through spectroscopic assay techniques, the mark needs to remain in proximity to the surface of the article, where it can effectively interact with incoming electromagnetic radiation.

In electrical measurements of identifying marks, carbon nanomaterials also are advantageous by offering the ready opportunity to change the electrical conductivity of the mark. In some implementations, the electrical conductivity of an identifying mark can be changed by altering the mass of carbon nanomaterial per unit area, but without substantially altering the "footprint" of the mark. For example, the number of carbon nanomaterial layers in a mark can be increased to enhance the mark's electrical conductivity without changing the apparent geometry (i.e., shape) of the mark. Functionalization of the carbon nanomaterial, combining two or more different types of carbon nanomaterials together, and/or combining other carbonaceous materials with the carbon nanomaterial can similarly be used to tailor the electrical conductivity of the mark to a desired degree without otherwise altering its apparent geometry.

Since electrical conductivity is a feature of many types of articles, electrically conductive marks can also be incorporated into the essential workings of an article. For example, an electrically conductive mark formed from a carbon nanomaterial can define at least a portion of a conductive line or circuit in an article. During a tampering event, if an outside entity breaks a conductive line defined by the identifying mark, the article can be configured to cease its proper function. In one implementation, an electrically conductive mark can be disposed between the surface of an article and an essential component of the article. If an outside entity attempts to gain unauthorized access to the essential component, access would necessarily take place by removing or destroying the mark. By coupling the mark to the workings of the article, the article can be configured to cease its proper functioning if damage to the mark occurs. Again, this represents another advantageous feature of the marks described herein.

Spectroscopic interrogation techniques are at least complementary to electrical interrogation techniques and can offer another level of authentication to the owner of an article. Additionally, spectroscopic interrogation techniques are more compatible with electrically conductive matrix materials. In another implementation, spectroscopic interrogation techniques can be used to authenticate an identifying mark in proximity to the surface of an article, and electrical interrogation techniques can be used to authenticate an identifying mark buried within the article. A further discussion of spectroscopic interrogation techniques and their advantages in authenticating an identifying mark follows hereinafter.

The spectroscopic properties of carbon nanotubes vary in an identifiable manner based upon, among other features, their chirality, thereby allowing a carbon nanotube spectrum to be resolved into both the types and abundances of the various carbon nanotube chiralities that are present in a sample. Carbon nanotube chirality refers to the orientation of carbon-carbon bonds within a carbon nanotube, as described in more detail below. By providing a population of carbon nanotubes with a known or registered distribution of carbon nanotube chiralities, an identifying mark can be produced therefrom with a unique spectral fingerprint that is very difficult for an outside entity to replicate, even if they know that carbon nanotubes are present in the article at all. In this regard, carbon nanotube synthetic conditions can often be varied to alter the distribution of carbon nanotube chiralities obtained, thereby offering the opportunity to tailor the spectral fingerprint of an identifying mark formed therefrom in a manner that may only be known and/or reproduced by an authorized entity. In another aspect, designed populations of carbon nanotubes can be formulated by combining carbon nanotubes from different carbon nanotube synthetic processes, thereby providing access to custom chirality distributions that may not be attainable directly from a single carbon nanotube synthetic process. In still another aspect, a population of carbon nanotubes can be treated to remove certain carbon nanotube chiralities following a carbon nanotube synthesis, thereby enriching the population of carbon nanotubes in the remaining chiralities. The removed carbon nanotubes can be similarly enriched in one or more chiralities. Functionalization of the carbon nanotubes can also be used to further tailor the spectral properties as needed. In summary, numerous options are available to render a population of carbon nanotubes difficult to replicate by an outside entity attempting to form an identifying mark therefrom.

Even if the size, shape and location of an identifying mark containing carbon nanotubes is determined and replicated by an outside entity, it can still be exceedingly difficult for the outside entity to precisely match the specific distribution of carbon nanotube chiralities that is present in the mark. For example, an outside entity might attempt to replicate an identifying mark to contain a like percentage of carbon nanotubes having a dominant chirality, but in doing so, it may not be possible for the outside entity to match the percent abundance of another type of carbon nanotube having a different chirality. That is, without knowing how the population of carbon nanotubes in the identifying mark was formed or further processed, it can be difficult for an outside entity to replicate the relative abundances of various carbon nanotube chiralities within the mark.

As a further advantage of carbon nanotubes in marking applications, carbon nanotubes are commonly present in various articles to take advantage of the enhancements conveyed by their mechanical, electrical and thermal properties. That is, the presence of carbon nanotubes in certain types of articles is not to be unexpected, and it can be difficult for the outside entity to even locate the mark at all. Thus, in some embodiments, an identifying mark formed from carbon nanotubes with a registered distribution of chiralities can be effectively "hidden" within another population of carbon nanotubes having either unregistered chiralities or a different distribution of chiralities compared to the identifying mark. Similarly, an identifying mark formed from carbon nanotubes can be effectively "hidden" within other carbonaceous materials such as graphene, diamond, polymers, polyaromatic hydrocarbons and the like. Carbon nanomaterials other than carbon nanotubes can also provide similar advantages in this regard. Only by locating the "hidden" identifying mark and conducting detailed analyses of it would an outside entity potentially come to realize its true purpose. Even then, replication of such identifying marks can be difficult for the reasons discussed herein. Further, as noted above, the identifying marks described herein are not considered to be visible to the naked eye, so they can be effectively "hidden" in plain sight.

In addition to producing identifying marks with a unique spectral fingerprint through tailoring of the chirality distribution, carbon nanotubes also offer significant advantages due to their extreme detection sensitivity. Fluorescence spectroscopy and Raman spectroscopy, the two spectral techniques most often used for determining carbon nanotube chiralities, are extremely sensitive when used for detecting carbon nanotubes. As a result, identifying marks containing very low carbon nanotube levels can be applied to an article and still remain detectable, even if the identifying mark is not visible to the naked eye. Identifying marks of very small physical dimensions can also provide like advantages.

Similar to fluorescence and Raman spectroscopies, the non-linear optical properties of carbon nanotubes can be used for assaying the particular characteristics of a population of carbon nanotubes. Specifically, by impinging a first wavelength of electromagnetic radiation upon the carbon nanotubes and receiving a second wavelength of altered frequency from the carbon nanotubes, it can be determined what types of carbon nanotubes are present by measuring the frequency shift. Thus, by making use of the non-linear optical properties of carbon nanotubes, an identifying mark with a distinctive spectral signature characteristic of the carbon nanotubes therein can similarly be obtained.

In additional embodiments, various addends can also be included in the carbon nanotubes or other carbon nanomaterial to convey a characteristic reflectivity signature to the identifying mark. Further, the carbon nanotubes or other carbon nanomaterials in the identifying mark can also be patterned, if desired, to create a frequency selective surface that can act as an optical bandpass filter during its interrogation with electromagnetic radiation. Either of these features can convey an additional level of security to the identifying marks. Even if the identifying mark is not patterned to create a frequency selective surface or some other functional feature, the pattern itself can represent a security feature of the mark that is known only to an authorized entity. In general, the identifying marks described herein can be patterned into any regular or irregular geometric shape or combination thereof.

Finally, identifying marks containing carbon nanotubes or other carbon nanomaterials can be either active or passive within an article in which they provide their tagging function. In passive tagging applications, the carbon nanotubes or carbon nanomaterials do not meaningfully contribute to the operational function of the article and only serve as a detectable identifying mark. In active tagging applications, such as those described above, the carbon nanotubes or carbon nanomaterials can provide at least one additional function within the article in addition to their tagging function. For example, an active mark can contribute to structural reinforcement within at least a portion of an article, or an active mark can constitute at least a portion of an electrically conductive pathway within an article. When serving within an electrically conductive pathway, tailoring of the distribution of carbon nanotube chiralities within the mark can also alter the operational function of the article, if desired. For example, depending upon if one wants to produce a conductive or semiconductive electrical connection within an article, one can formulate a population of carbon nanotubes to have chiralities that lead to either semiconducting or metallic conductivity. The opportunity to alter the operational function of an article without visually changing its appearance can convey another level of tamper resistance thereto.

As used herein, the term "identifying mark" or just "mark" refers to a region that contains a carbon nanomaterial upon or within an article, such that the carbon nanomaterial can be optically or electrically interrogated to receive a signal therefrom. Within the context of the present embodiments, marks are not particularly limited in size, shape, thickness, or the like, unless otherwise indicated herein. In various embodiments, the marks described herein can be "invisible" or "not visible to the naked eye." In alternative embodiments, however, such marks can remain visible to the naked eye.

As used herein, the terms "optically interrogate" or "spectroscopically interrogate" and variants thereof refer to the interaction of electromagnetic radiation of any wavelength with a carbon nanomaterial and receipt and analysis of the electromagnetic radiation thereafter.

As used herein, the term "electrically interrogate" and variants thereof refer to the influence of an identifying mark containing a carbon nanomaterial on an electronic output signal received from the mark. In illustrative embodiments, the electronic signal can result from passage of an electric current through the mark or through interaction of the mark with an electrical field.

As used herein, the term "not visible to the naked eye" refers to a mark that cannot be seen with the human eye under ordinary circumstances, including through optical enhancement, such as with a microscope or like optical magnifier. For the purposes of this disclosure, identifying marks that cannot be seen with an optical microscope under ordinary circumstances will be considered to be "not visible to the naked eye." Identifying marks that are not visible to the naked eye can be "spectroscopically identifiable" or "electrically identifiable," however, as discussed further herein.

As used herein, the term "registered distribution of chiralities" refers to a population of carbon nanotubes having a chirality distribution that is known to a limited number of entities, but is unknown to an outside entity.

As used herein, the term "carbon nanotube chirality" refers to a double index (n,m) describing a particular carbon nanotube, where n and m are integers that describe the cut and wrapping of hexagonal graphite when formed into a tubular structure. Such designation of a carbon nanotube's chirality will be familiar to one having ordinary skill in the art. As used herein, the term "semiconducting carbon nanotube" refers to a carbon nanotube that is defined by the relationship $|m-n|=3k+1$, where k is an integer. As used herein, the term "metallic carbon nanotube" refers to a carbon nanotubes that is defined by the relationship $|m-n|=3k$, where k is an integer. According to the embodiments of the present disclosure, metallic carbon nanotubes and semi-metallic carbon nanotubes will be considered to be synonymous with one another. Carbon nanotubes may be further characterized as being "zig-zag chirality" or "armchair chirality" based upon their chiral indices. For example, metallic carbon nanotubes having m=n are characterized as "armchair chirality" carbon nanotubes.

As used herein, the term "operationally deploying" refers to the condition that exists when an article is released from its manufacturer's control. In some embodiments, an article can be considered to be operationally deployed when the article is passed from a manufacturer to a retailer or wholesaler, or directly provided to a consumer or industrial project. In some or other embodiments, an article can be considered to be operationally deployed when the article is situated in its intended operational location. In any event, a manufacturer or other entity may wish to interrogate the article after its deployment in order to verify the article's authenticity. Not only can such analyses help a manufacturer identify counterfeit articles, but they can also provide improved consumer safety by identifying counterfeit articles that are deployed in various mission-critical situations.

As used herein, the term "non-native distribution of chiralities" refers to a chirality distribution that is generally not attainable directly from a carbon nanotube synthetic process.

As used herein, the term "tracking" refers to a process of identification or authentication. The terms "tagging," "tracking" and related variants thereof may be used synonymously herein.

As used herein, the term "substantially non-conductive matrix material" refers to a support material upon which or within which an identifying mark is disposed, wherein the matrix material has a resistance that is at least about 1000 times greater than that of the identifying mark.

As used herein, the term "bulk conductivity" refers to the conductivity of a matrix material on the macroscale, as opposed to the localized electrical conductivity that can occur in proximity to an identifying mark.

As used herein, the term "resonant communication" refers to the conveyance of an electromagnetic signal across a spatial separation from a first identifying mark containing a first carbon nanomaterial to a second identifying mark containing a second carbon nanomaterial.

As used herein, the term "localized" refers to the condition of an identifying mark being present in only a portion of an article.

In some embodiments, articles described herein can include an identifying mark that is not visible to the naked eye, where the identifying mark contains a carbon nanomaterial that includes a plurality of carbon nanotubes having a registered distribution of chiralities. Such identifying marks can be optically interrogated in order to authenticate the mark. FIG. 1 shows a series of illustrative Raman spectra of various carbon nanotube samples that differ slightly in their chiral distribution. As can be seen in FIG. 1, slight spectral shifts can be observed, and the spectral peaks can be differentiated from those of graphite.

In some embodiments, articles described herein can include an identifying mark that is localized and not visible to the naked eye, where the identifying mark is electrically conductive and contains a carbon nanomaterial. Such identifying marks can be electrically interrogated, such as through measuring eddy currents or resonant communication within the article.

In some embodiments, the identifying mark can include substantially a monolayer of a carbon nanomaterial on a surface of the article. A monolayer of a carbon nanomaterial is not visible to the naked eye but can remain detectable by various spectroscopic and electrical interrogation techniques. Thicker carbon nanomaterial layers can also remain invisible to the naked eye and can be used in some embodiments of the present disclosure, particularly if the identifying mark is to be electrically interrogated. For example, by including a greater amount of an electrically conductive carbon nanomaterial per unit area within the identifying mark, the mark's electrical conductivity can be increased, thereby enhancing its eddy current signature. Such electrically conductive marks can be buried within an article in order to prevent them from being visually observable.

In some embodiments, the identifying mark can remain invisible to the naked eye due to a coating that covers at least the identifying mark of the article. Suitable coatings are described in more detail below. In some embodiments, the article itself or the coating can further include another carbonaceous material which can also mask the presence of the carbon nanotubes or other carbon nanomaterial and render them not visible to the naked eye. Carbonaceous materials that can mask the presence of carbon nanotubes can include, for example, graphite, graphene, amorphous carbon, carbon black, polymers, polyaromatic hydrocarbons, and the like. Some of these entities can be used to further tailor the spectral signature produced by the identifying mark, as shown in FIGS. 3A-3C and 4A-4C below. When the identifying mark is to be spectroscopically interrogated, the material forming the coating is selected to be sufficiently transparent to incoming electromagnetic radiation to allow the mark to be effectively assayed by the electromagnetic radiation. The coating thickness can also influence its optical transparency. One of ordinary skill in the art will be able to identify materials that are suitably transparent to a particular type or wavelength of electromagnetic radiation in order to practice the embodiments of the present disclosure. In contrast, when the identifying mark is to be electrically interrogated, the material forming the coating is not believed to be particularly limited.

As indicated above, identifying marks to be spectroscopically interrogated are usually placed in proximity to the surface of the article, although surface marks can also be electrically interrogated according to the embodiments of the present disclosure. In general, carbon nanotubes and other carbon nanomaterials adhere fairly readily to a variety of surface types. Accordingly, the types of articles that can be marked according to the embodiments described herein are not believed to be particularly limited. Illustrative articles that can be marked by applying carbon nanotubes having a registered distribution of chiralities to a surface of the article include, for example, electrical devices, circuit boards, jewelry, automobiles, medical devices, sporting goods, structural components, mirrors, lenses, optical filters, various components thereof, and the like. In some embodiments, the identifying mark can be applied to the article itself, and in other embodiments, the identifying mark can be applied to the packaging in which one or more articles are being shipped or housed. In still other embodiments, the identifying mark can be incorporated within the article itself, particularly when the identifying mark is to be electrically interrogated. For example, a "subsurface" or "buried" identifying mark within an article can be electrically interrogated in order to authenticate the mark.

Although any type of article can be marked according to the embodiments described herein, it is believed that marking of electrical devices can be particularly advantageous. As indicated above, many types of electrical devices containing carbon nanotubes and other electrically conductive carbon nanomaterials are in development. Thus, an identifying mark containing a carbon nanomaterial, either visible or non-visible, can be incorporated within such devices without significantly alerting an outside entity of the mark's presence. For example, an identifying mark having a registered distribution of carbon nanotube chiralities can be incorporated within a larger population of carbon nanotubes with a different chirality distribution, which may or may not be used to alter the operational principles of the electrical device. In such embodiments, the identifying mark can be electrically isolated from the larger population of carbon nanotubes, electrically connected to the larger population of carbon nanotubes without changing the operational principles of the electrical device (i.e., as a "dummy" electrical pathway), or overlay a portion of the larger population of carbon nanotubes in an electrical circuit. In the latter configuration, the region of the electrical circuit containing the identifying mark can only be distinguished from the remainder of the electrical circuit by knowing the location of the mark and determining its unique spectral signature. In still further configurations, the identifying mark can itself contribute to the electrical operational principles of the device by establishing a conductive or semiconductive pathway therein based on the particular carbon nanotube chirality distribution that is present in the mark. Thus, in some embodiments, an identifying mark formed from carbon nanotubes can be used to establish "invisible" electrical connections within an electrical device in order to mask the device's true electrical operational principles, thereby making reverse engineering much more difficult for an outside entity. The identifying mark's geometric shape can also provide a further level of authentication to an authorized entity.

Similarly, an electrically conductive identifying mark that does not contain a registered distribution of carbon nanotube chiralities can also be used for marking an article. Suitable carbon nanomaterials for inclusion in an identifying mark to be electrically interrogated can include carbon nanotubes, graphene, any functionalized variant thereof, or any combination thereof. Carbon nanotubes in an identifying mark to be electrically interrogated need not necessarily have any particular chirality distribution, although they can have a registered chirality distribution in some embodiments. By electrically interrogating an article containing an electrically conductive identifying mark, one can determine if one or more identifying marks are present in the proper location(s) within the article, are of the proper shape(s), and have the proper conductivities to induce the correct eddy current signatures within the articles. In addition, in embodiments where the identifying mark also contains a registered distribution of carbon nanotube chiralities, the results of spectroscopic interrogation can be compared to that obtained from the electrical interrogation technique to provide an additional level of security to the mark.

In some embodiments, the article can include an electrical device containing an electronic component. The type of electrical device being marked with a carbon nanomaterial according to the present embodiments is not believed to be particularly limited. For example, in various embodiments, the electrical device can include a two-terminal electrical device or a three-terminal device (e.g., a gated electrical device). In some embodiments, the carbon nanomaterial can constitute at least a portion of a conductive line in a circuit of the electrical device. That is, in some embodiments, the identifying mark can be in electrical communication with the electronic component of the electrical device. In some embodiments, the conductive line can be formed entirely with carbon nanotubes having a registered distribution of chiralities, and in other embodiments, one or more separated regions of the conductive line can be formed with carbon nanotubes having a registered distribution of chiralities. In other embodiments, the conductive line can be formed from a carbon nanomaterial that lacks carbon nanotubes having a registered distribution of chiralities. In still other embodiments, an identifying mark in an electrical device can be electrically isolated from an electronic component therein. In any of the foregoing configurations, electrical interrogation, spectroscopic interrogation, or any combination thereof can be used in authenticating the identifying mark.

A plurality of carbon nanotubes having a registered distribution of chiralities used in the identifying marks of the present disclosure can be produced by any suitable technique. Suitable carbon nanotube synthetic processes can include, for example, arc methods, laser oven, chemical vapor deposition, flame synthesis, and high pressure carbon monoxide (HiPCO). The synthetic conditions of any of these techniques can be altered to change the chirality distribution produced, particularly to favor the production of carbon nanotubes with a dominant carbon nanotube chirality or type being produced.

In some embodiments, the plurality of carbon nanotubes in the identifying mark can constitute as-produced carbon nanotubes obtained from a carbon nanotube synthetic process. As discussed above, one practicing the embodiments described herein can choose carbon nanotubes produced by a particular carbon nanotube synthetic process based upon the distribution of carbon nanotube chiralities obtained under a specific set of carbon nanotube synthetic conditions. Optionally, the carbon nanotubes can be further purified, such as by acid treatment to remove at least a portion of a residual transition metal carbon nanotube growth catalyst from the carbon nanotubes. In some embodiments, an amount of residual transition metal carbon nanotube growth catalyst within an identifying mark can be determined and compared against the value of this quantity in the carbon nanotubes used to apply the mark to an article. Thus, analysis of the residual transition metal carbon nanotube growth catalyst within an identifying mark can serve as a secondary level of authentication in addition to the distribution of carbon nanotube chiralities.

In some or other embodiments, the plurality of carbon nanotubes having a registered distribution of chiralities can include a mixture of carbon nanotubes combined from a first carbon nanotube synthetic process and a second carbon nanotube synthetic process, where the first and second carbon nanotube synthetic processes produce carbon nanotubes that differ in at least their distribution of chiralities. That is, the plurality of carbon nanotubes having a registered distribution of chiralities can be formed by combining, in any ratio, two different batches of carbon nanotubes, each with its own unique chirality distribution. For example, a first carbon nanotube synthetic process may produce a majority amount of a first carbon nanotube chirality [e.g., (6,5) chirality] and lower amounts of one or more second carbon nanotube chiralities [e.g., (7,5) and (8,4) chiralities], and a second carbon nanotube synthetic process may produce a majority amount of one or more of the second carbon nanotube chiralities or a different set of carbon nanotube chiralities entirely. By combining carbon nanotubes from the first and second carbon nanotube synthetic processes, a plurality of carbon nanotubes having a distinctive chirality signature can be formulated for preparing an identifying mark. Such chirality signatures may not be directly obtainable from a single carbon nanotube synthetic process. Further, by varying the ratios of the carbon nanotubes being combined from each carbon nanotube synthetic process, the relative abundance of the various carbon nanotube chiralities to one another can be further tailored. In various embodiments, an amount of carbon nanotubes being combined from each carbon nanotube synthetic process can represent about 10% or more of the mixture, more typically about 20% or more. In some embodiments, carbon nanotubes from three or more different carbon nanotube synthetic processes can be combined with one another in a like manner.

In still other embodiments, the plurality of carbon nanotubes can include carbon nanotubes having one or more chiralities that have been enriched from as-produced carbon nanotubes obtained from a carbon nanotube synthetic process. Enrichment of particular types or chiralities of carbon nanotubes can be accomplished in various ways. In some embodiments, separation techniques based on the electrical properties of the carbon nanotubes can be used to affect separation. For example, electrophoresis can be used to separate metallic carbon nanotubes from semiconducting carbon nanotubes. Density gradient chromatography can be used similarly to separate carbon nanotubes having various chiralities from one another. Either the separated carbon nanotubes or the residual carbon nanotubes depleted of particular chiralities can be used in accordance with the embodiments described herein. In some embodiments, separating particular carbon nanotube chiralities from one another can involve selectively functionalizing carbon nanotubes having certain chiralities within a population of as-produced carbon nanotubes. For example, by controlling the reactive stoichiometry, metallic carbon nanotubes can be functionalized in preference to semiconducting carbon nanotubes, thereby allowing the two types of carbon nanotubes to be at least partially separated from one another based upon the change in properties that occur following functionalization (e.g., solubility). Some illustrative carbon nanotube functionalization techniques are discussed below. Combinations of the foregoing separation techniques can be used as well.

Techniques similar to those described above can also be used to produce carbon nanotubes for use in identifying marks configured for authentication by electrical interrogation techniques. That is, similar carbon nanotube synthesis techniques can be used to produce carbon nanotubes for inclusion in an identifying mark when it is not particularly important to know the distribution of carbon nanotube chiralities. In still other embodiments, a registered distribution of carbon nanotube chiralities can be present in an identifying mark, even if the mark is being authenticated through electrical interrogation techniques. As indicated previously, spectroscopic interrogation of such marks can provide an additional level of authentication to that provided by the electrical interrogation techniques.

Techniques used for producing graphene for inclusion within the identifying marks of the present disclosure are similarly not believed to be particularly limited. Suitable graphene synthesis techniques can include, for example, CVD synthesis, graphite exfoliation and reduction, epitaxial growth, and any combination thereof.

In some embodiments, the carbon nanomaterial forming the identifying mark can be functionalized. The type of functionalization on the carbon nanomaterial is not believed to be particularly limited. Illustrative carbon nanotube functionalization techniques will be familiar to one having ordinary skill in the art. In some embodiments, functionalization can be used to facilitate at least partial separation of different carbon nanotube types from one another, as alluded to above. Specifically, in some embodiments, metallic and semi-metallic carbon nanotubes can be functionalized with an electrophile (e.g., with a diazonium moiety as described in U.S. Pat. No. 7,572,426, which is incorporated herein by reference in its entirety) in preference to semiconducting carbon nanotubes and undergo separation from the latter based on one or more property changes following functionalization. In other embodiments, the different carbon nanotube types can be functionalized with the same functionalizing species in a non-specific manner, although not necessarily with the same degree of functionalization. In still other embodiments, semiconducting carbon nanotubes can be differentially functionalized from metallic carbon nanotubes in a plurality of carbon nanotubes used for forming an identifying mark. That is, in some embodiments, metallic carbon nanotubes can be reacted initially with a first functionalizing species, and the semiconducting carbon nanotubes can thereafter be reacted with a second functionalizing species. As indicated above, in some embodiments, the semiconducting carbon nanotubes can be separated from the functionalized metallic carbon nanotubes before or after undergoing functionalization with the second functionalizing species. Functionalized semiconducting carbon nanotubes can be recombined with metallic carbon nanotubes functionalized with the first functionalizing species, or they can be recombined with other metallic carbon nanotubes (including unfunctionalized metallic carbon nanotubes) or semiconducting carbon nanotubes (including unfunctionalized semiconducting carbon nanotubes) in some embodiments.

Figure 2A:
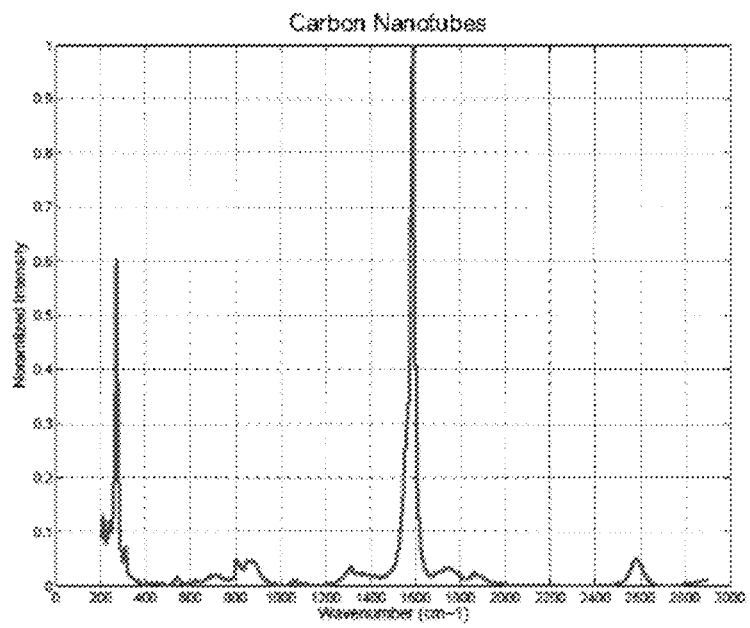
FIGS. 2A and 2B show a comparison between illustrative Raman spectra for unfunctionalized carbon nanotubes and those that have been functionalized with tetracyanoquinodimethane (TCNQ)
Figure 2B:
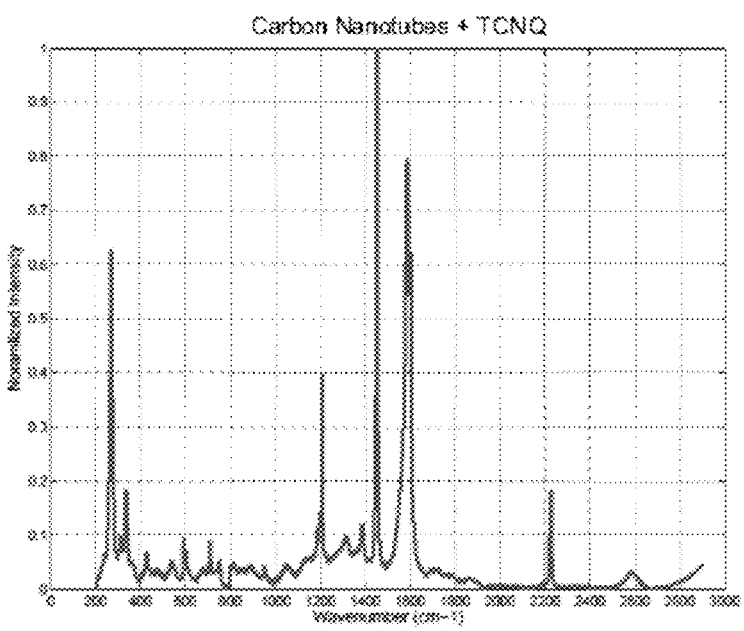

In some or other embodiments, functionalization of carbon nanotubes need not necessarily be used to separate carbon nanotube types from one another or even be specific to a particular type of carbon nanotube. In some embodiments, additional processing of the carbon nanotubes can take place to affect functionalization of the carbon nanotubes, such as plasma exposures and other relatively non-specific functionalization strategies. When performed, functionalization can take place on the ends of the carbon nanotubes, the sidewalls of the carbon nanotubes, or both. As an illustrative carbon nanotube functionalization technique, carbon nanotube ends can be opened through treatment with an appropriate oxidizing agent (e.g., $HNO_3/H_2SO_4$) to generate carboxylic acid-functionalized carbon nanotubes. Functionalization can change the spectral properties of the carbon nanotubes and shift the spectral fingerprint observed in an identifying mark formed therefrom, thereby providing a further variable that an outside entity would need to replicate in forming a counterfeit mark. For example, FIGS. 2A and 2B show a comparison between illustrative Raman spectra for unfunctionalized carbon nanotubes and those that have been functionalized with tetracyanoquinodimethane (TCNQ). As can be seen in FIG. 2B, the TCNQ peaks are prevalent in the spectrum, and the lower intensity carbon nanotube peaks have disappeared or shifted as well. One of ordinary skill in the art will further recognize that functionalization can also alter the electrical properties of carbon nanotubes, such that the electrical signature of an identifying mark formed therefrom can be tailored to a desired degree.

Graphene used in an identifying mark can be functionalized in a similar manner to carbon nanotubes. Again, suitable graphene functionalization techniques will be familiar to one having ordinary skill in the art. The graphene can be functionalized within the $sp^2$ carbon basal plane of the graphene or on the residual functional groups located about the periphery of the graphene. Peripheral functional groups in graphene that can be functionalized through any suitable technique include, for example, carboxylic acids, hydroxyl groups, carbonyl groups, and epoxides. In some instances, the carbon nanotube functionalization techniques described above can be extended to graphene functionalization, particularly for functionalizing the graphene basal plane. In other embodiments, the peripheral functional groups in graphene can be functionalized (e.g., through esterification, amidation, etherification, nucleophilic epoxide opening, and the like) to produce a graphene having a desired set of properties. In some embodiments, functionalization of the graphene can be used to tailor its electrical conductivity to a desired degree for inclusion in an electrically conductive identifying mark.

As indicated above, the particular process conditions used for preparing a batch of carbon nanotubes can often result in certain carbon nanotube chiralities being predominant, as well as differing relative abundances of the various carbon nanotube chiralities with respect to one another. It should be noted, however, that the presence of a predominant type or abundance of carbon nanotube in the identifying mark is not needed to practice the embodiments of the present disclosure, simply that the distribution of carbon nanotube chiralities is known for an identifying mark to be authenticated through spectroscopic interrogation techniques. However, in some embodiments, the plurality of carbon nanotubes can have one or more predominant types of carbon nanotubes, as this feature can prove advantageous for spectroscopic interrogation. Various configurations in which the plurality of carbon nanotubes includes a predominant carbon nanotube type are discussed below.

The native distribution of carbon nanotube types in a non-specific carbon nanotube synthetic process is usually about 2/3 semiconducting carbon nanotubes and about 1/3 metallic carbon nanotubes. In some embodiments, the plurality of carbon nanotubes forming the identifying mark can have a higher percentage of semiconducting carbon nanotubes than is natively obtained from a non-specific carbon nanotube synthetic process. Illustrative techniques for producing enriched semiconducting carbon nanotubes are discussed above. In some embodiments, the plurality of carbon nanotubes can include about 70% semiconducting carbon nanotubes or more. In other various embodiments, the plurality of carbon nanotubes can include about 75% semiconducting carbon nanotubes or more, or about 80% semiconducting carbon nanotubes or more, or about 85% semiconducting carbon nanotubes or more, or about 90% semiconducting carbon nanotubes or more, or about 95% semiconducting carbon nanotubes or more. In some embodiments, the plurality of carbon nanotubes can include substantially only semiconducting carbon nanotubes. Illustrative semiconducting carbon nanotube chiralities that can be present in the identifying marks of the present disclosure include, for example, (1,0), (2,0), (4,0), (5,0), (7,0), (8,0), (10,0), (11,0), (13,0), (14,0), (16,0), (2,1), (3,1), (5,1), (6,1), (8,1), (9,1), (11,1), (12,1), (14,1), (15,1), (3,2), (4,2), (6,2), (7,2), (9,2), (10,2), (12,2), (13,2), (15,2), (4,3), (5,3), (7,3), (8,3), (10,3), (11,3), (13,3), (14,3), (5,4), (6,4), (8,4), (9,4), (11,4), (12,4), (14,4), (6,5), (7,5), (9,5), (10,5), (12,5), (13,5), (7,6), (8,6), (10,6), (11,6), (13,6), (8,7), (9,7), (11,7), (12,7), (9,8), (10,8), (12,8), (10,9), (11,9), and (11,10). Certain chiralities can be predominant in some carbon nanotube synthetic processes, as discussed in more detail below.

Likewise, in some embodiments, the plurality of carbon nanotubes can include a higher percentage of metallic carbon nanotubes than is natively obtained from a non-specific carbon nanotube synthetic process. In some embodiments, the plurality of carbon nanotubes can include about 50% metallic carbon nanotubes or more. In other various embodiments, the plurality of carbon nanotubes can include about 60% metallic carbon nanotubes or more, or about 70% metallic carbon nanotubes or more, or about 80% metallic carbon nanotubes or more, or about 90% metallic carbon nanotubes or more. In some embodiments, the plurality of carbon nanotubes can include substantially only metallic carbon nanotubes. In some embodiments, the plurality of carbon nanotubes can include substantially only functionalized metallic carbon nanotubes. Illustrative metallic carbon nanotubes that can be present in the identifying marks of the present disclosure include, for example, (3,0), (6,0), (9,0), (12,0), (15,0), (4,1), (7,1), (10,1), (13,1), (5,2), (8,2), (11,2), (14,2), (6,3), (9,3), (12,3), (7,4), (10,4), (13,4), (8,5), (11,5), (9,6), (12,6), (10,7), and (11,8).

As discussed above, it is not a necessary feature that the plurality of carbon nanotubes forming an identifying mark for spectroscopic interrogation contains one or more predominant types of carbon nanotubes, simply that the plurality of carbon nanotubes has a registered distribution of carbon nanotube chiralities, where the abundances of one or more chiralities are known. However, in some embodiments, it can be desirable that the plurality of carbon nanotubes contains one or more carbon nanotube chiralities in a defined excess relative to the other carbon nanotube chiralities. By having one or more types of carbon nanotubes present in a significant abundance over the others, increased signal strength can result in improved detection sensitivity and accuracy (e.g., in a fluorescence spectrum or a Raman spectrum of the identifying mark).

In more specific embodiments, the identifying mark can contain a plurality of carbon nanotubes in which at least about 30% of the carbon nanotubes are of a single chirality. In some embodiments, at least about 50% of the carbon nanotubes can be of a single chirality, or at least about 70% of the carbon nanotubes can be of a single chirality. In some embodiments, the plurality of carbon nanotubes can contain a mixture of semiconducting and metallic carbon nanotubes in which a single chirality is present within the above ranges of abundance. In other various embodiments, the plurality of carbon nanotubes can include substantially only semiconducting carbon nanotubes or substantially only metallic carbon nanotubes in which a single chirality is present within the above ranges of abundance. The single carbon nanotube chirality that is present in the above ranges of abundance is not believed to be particularly limited, but can represent a carbon nanotube chirality that is readily produced in a particular carbon nanotube synthetic process. Illustrative carbon nanotube chiralities that can represent a predominant chirality in this regard include, for example, (6,5), (7,5), and (8,4) chiralities. In an illustrative embodiment, the plurality of carbon nanotubes can be a commercial carbon nanotube product containing about 90-97% semiconducting carbon nanotubes, which includes about 30-45% (6,5) carbon nanotubes and smaller quantities of (7,5) and (8,4) carbon nanotubes. Such a population of carbon nanotubes is available from SouthWest Nanotubes (Norman, Okla.) as product SG65i. In another illustrative embodiment, the plurality of carbon nanotubes can be a commercial carbon nanotube product containing greater than about 50% semiconducting carbon nanotubes of (7,6) chirality. Such a population of carbon nanotubes is available from SouthWest Nanotubes as product SG76. As discussed above, these carbon nanotube products can be used directly to form identifying marks, or they can be combined in any ratio to create a chirality distribution that is not found in either product. Other strategies for manipulating the distribution of carbon nanotube chiralities are discussed in further detail above. Other techniques for adjusting the spectroscopic signature of the identifying marks of the present disclosure are also described below.

Carbon nanotube lengths and diameters can also be varied as another parameter defining the identifying marks described herein. In some embodiments, an average length of the carbon nanotubes in the identifying mark can range between about 1 μm and about 500 μm, or between about 1 μm and about 10 μm, or between about 10 μm and about 100 μm, or between about 100 μm and about 200 μm, or between about 200 μm and about 300 μm, or between about 300 μm and about 400 μm, or between about 400 μm and about 500 μm. In other embodiments, the carbon nanotubes in the identifying mark can have an average length that is greater than about 500 μm, including, for example, between about 500 μm and about 700 μm, or between about 700 μm and about 1000 μm.

In some embodiments, the carbon nanotubes in the identifying mark can have diameters ranging between about 1 nm and about 20 nm. In more particular embodiments, the carbon nanotubes in the identifying mark can have diameters ranging between about 1 nm and about 10 nm, or between about 1 nm and about 7 nm, or between about 1 nm and about 5 nm, or between about 2 nm and about 6 nm, or between about 2 nm and about 5 nm, or between about 3 nm and about 8 nm. In some embodiments, the carbon nanotubes can be predominantly single-walled carbon nanotubes. In other embodiments, double-walled or multi-walled carbon nanotubes can be present. In some embodiments, mixtures of single-walled carbon nanotubes and double- or multi-walled carbon nanotubes can be used. In some embodiments, mixtures of two or more carbon nanotube types, each having different diameters, can be present in order to further tailor the spectroscopic fingerprint of the identifying marks described herein.

Semiconducting carbon nanotubes can be particularly desirable for use in conjunction with the embodiments described herein, since they are readily detectable in low abundance using fluorescence spectroscopy, and the frequency of the fluorescence is correlatable to the specific carbon nanotube chiralities that are present. Further details of the fluorescence properties of semiconducting carbon nanotubes and their associated chirality assignments can be found in Bachilo, et al., "Structure-assigned optical spectra of single-walled carbon nanotubes," Science, 298:2002, pp. 2361-2366.

Carbon nanotubes can also be readily detected and analyzed in the solid state using Raman spectroscopy, such as a microtiter plate format for rapid analyses. Unlike fluorescence spectroscopy, which is only workable for semiconducting carbon nanotubes, Raman spectroscopy can be used to detect and analyze both metallic and semiconducting carbon nanotubes. As with fluorescence spectroscopy, the excitation frequencies of a Raman spectrum can be correlated with the particular carbon nanotube chiralities that are present in the sample being analyzed. The diameters of the carbon nanotubes can also be readily determined from a Raman spectrum, and the carbon nanotube diameters in the identifying mark can serve as another level of security against unwanted counterfeiting by an outside entity. As mentioned above, optical reflectivity can also be used to provide an additional level of security in a similar manner.

As indicated above, the identifying marks described herein can contain a nanomaterial that includes a plurality of carbon nanotubes having a registered distribution of chiralities. Such identifying marks can be assayed by spectroscopic interrogation techniques, as well as by electrical interrogation techniques. In some embodiments, other carbon nanomaterials such as graphene, nanocarbon particles, or nanodiamond can be used in any combination with carbon nanotubes in the identifying marks described herein. In alternative embodiments, the foregoing nanomaterials can be used separately or in combination with one another, but without carbon nanotubes being present, to form an identifying mark with a distinctive spectral signature that makes the identifying mark spectroscopically identifiable. For example, in some embodiments, an identifying mark can be formed from graphene, nanodiamond, or a mixture of graphene and nanodiamond. One of ordinary skill in the art will recognize that these nanomaterials also possess characteristic spectral signatures that can be used to validate an identifying mark according to the embodiments described herein.

Electrically conductive identifying marks to be authenticated through electrical interrogation techniques need only contain an electrically conductive carbon nanomaterial. Accordingly, in some embodiments, the identifying mark can include carbon nanotubes, graphene, any functionalized variant thereof, or any combination thereof. In embodiments where carbon nanotubes are present, the carbon nanotubes can have a non-specified chirality distribution or they can have a registered distribution of chiralities. In some embodiments, the carbon nanomaterial of the identifying mark contains at least carbon nanotubes, and the carbon nanotubes have a registered distribution of chiralities. Such identifying marks can be interrogated through electrical techniques, spectroscopic techniques, or any combination thereof.

Figure 3A:
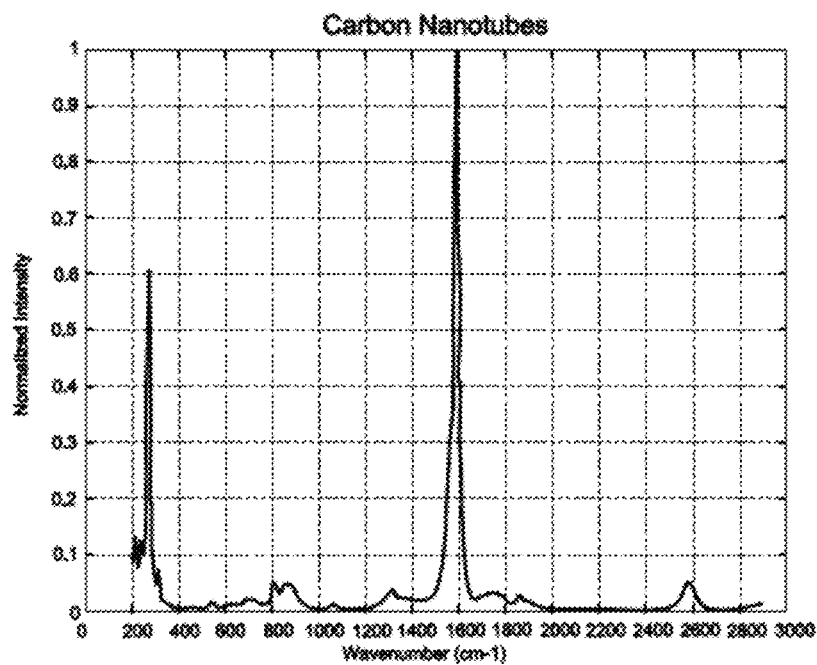
FIGS. 3A-3C show a comparison between illustrative Raman spectra for carbon nanotubes, rubrene (5,6,11,12-tetraphenyltetracene), and carbon nanotubes that have been mixed with rubrene.
Figure 3B:
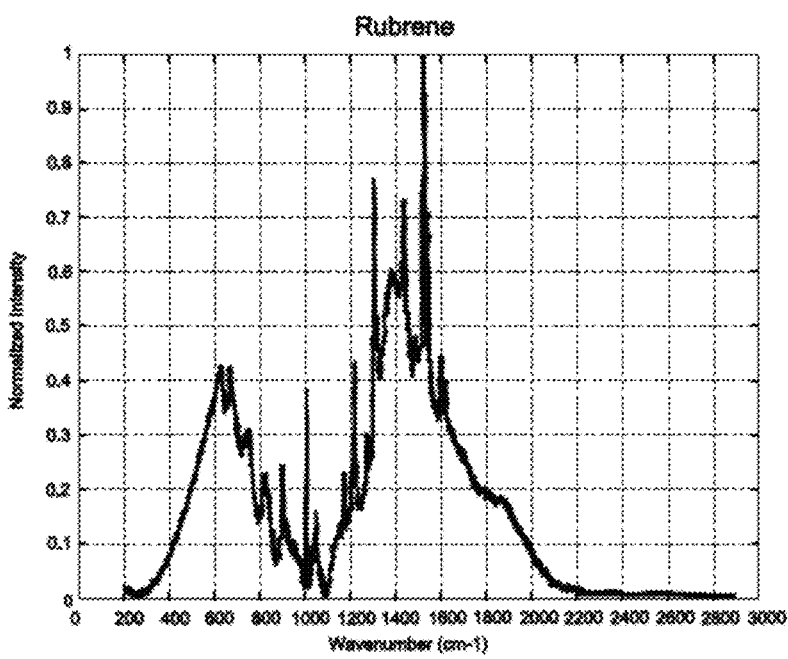
Figure 3C:
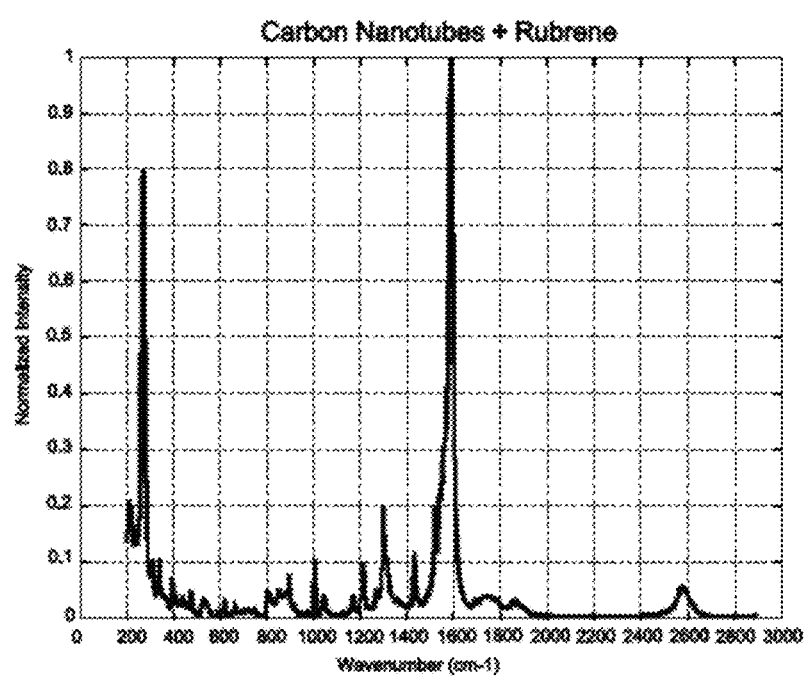
Figure 4A:
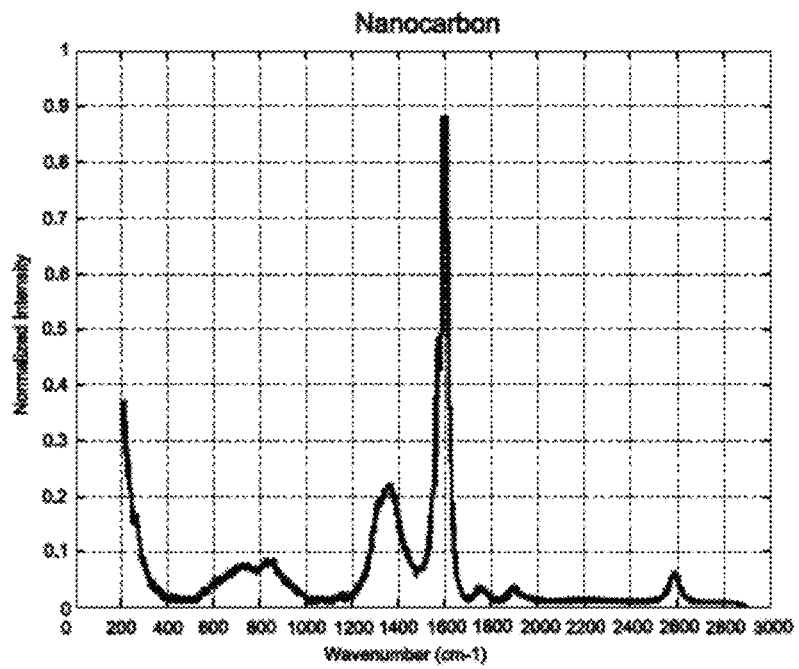
FIGS. 4A-4C show a comparison between illustrative Raman spectra for nanocarbon, rubrene, and nanocarbon mixed with rubrene.
Figure 4B:
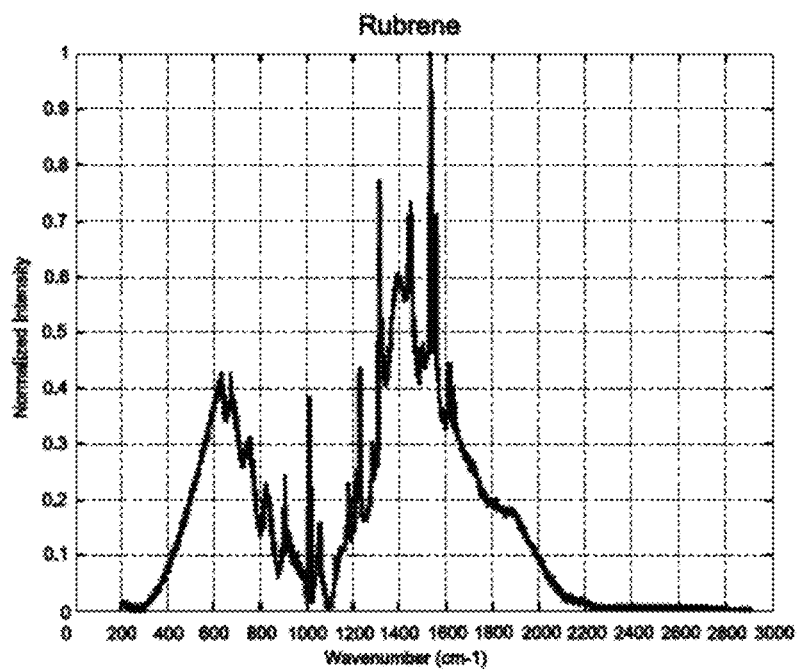
Figure 4C:
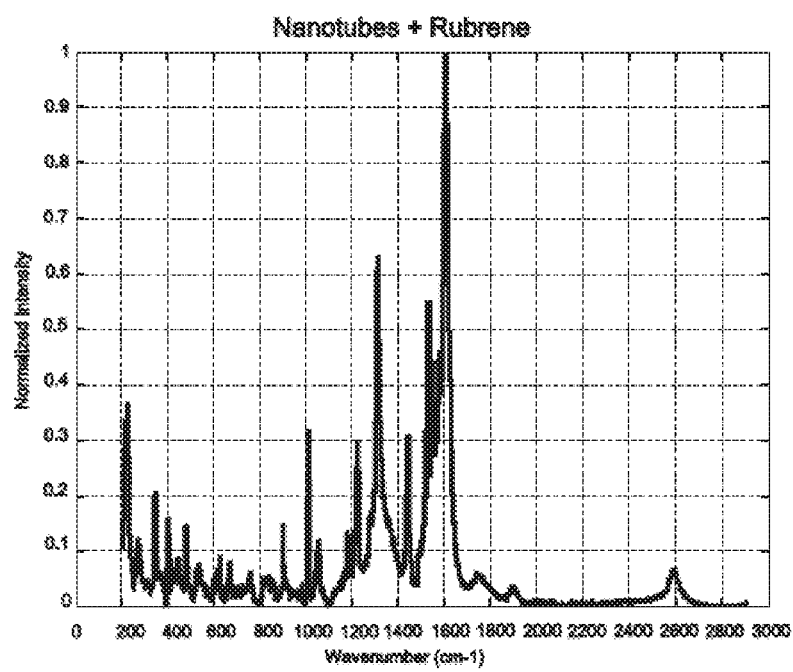

In addition to carbon nanomaterials, other carbonaceous materials can also be present in the identifying marks described herein. Suitable carbonaceous materials that can be included in the identifying marks described herein include, for example, graphite, various polymers, aromatic hydrocarbons, particularly polycyclic aromatic hydrocarbons, and the like. These materials can likewise be used to influence the spectral signature obtained from carbon nanotubes or another carbon nanomaterial. FIGS. 3A-3C show a comparison between illustrative Raman spectra for carbon nanotubes, rubrene (5,6,11,12-tetraphenyltetracene), and carbon nanotubes that have been mixed with rubrene. FIGS. 4A-4C similarly show a comparison between illustrative Raman spectra for nanocarbon, rubrene, and nanocarbon mixed with rubrene. As can be seen from the comparative spectra, the rubrene imparts a distinctive spectral signature that is not present in the undoped nanomaterial spectra. In addition, inclusion of other carbonaceous materials in the identifying mark can further influence the mark's electrical conductivity and alter the eddy current signature produced by the mark during electrical interrogation.

As an additional means of protecting the identifying marks described herein, both from the marks' external environment as well as unwanted investigation by an outside entity, the articles described herein can further include a coating covering at least the identifying mark. For identifying marks that are configured for spectroscopic interrogation, any at least partially spectroscopically transparent film that adheres to the article and prevents or inhibits damage to or reaction of the identifying mark, removal of the identifying mark, or investigation of the identifying mark can be used in accordance with the embodiments described herein. That is, coatings suitable for use in spectroscopic mark interrogation techniques can include any substance that is not appreciably Raman active or fluorescent, at least within the frequency range over which the carbon nanotubes in the identifying mark are Raman active or fluorescent. In contrast, when electrical interrogation techniques are used, the composition of a coating covering the mark is not believed to be particularly limited, provided that the coating is not substantially electrically conductive.

Various polymer films can be used as a coating on the articles described herein, a number of which will be familiar to one having ordinary skill in the art. Choice of a suitable polymer film for forming the coating can be dictated by factors including, for example, the degree to which the polymer film adheres to a particular article containing the identifying mark. Illustrative polymer films that can be used in conjunction with the embodiments described herein include, for example, polyimides, silicone polymers, polycarbonates, fluoropolymers such as polytetrafluoroethylene, and the like. In addition to protecting the identifying mark, as described above, the carbon present in the polymer film can further conceal the presence of carbon nanotubes in the article from an outside entity.

Due to the need for spectroscopic transparency, identifying marks to be spectroscopically interrogated are generally located in proximity to the surface of an article being marked. In contrast, identifying marks to be electrically interrogated are not particularly limited in their placement, provided that there is not a substantial amount of a conductive material intervening between the identifying mark and a detector interrogating the mark, such as an eddy current detector or probe. Accordingly, in more specific embodiments, an identifying mark intended for electrical interrogation can be located on or within a portion of a substantially non-conductive matrix material constituting the article being marked. Suitable matrix materials can include, for example, various polymers, glasses, ceramics and the like. Although electrically conductive nanomaterials, particularly carbon nanomaterials, have been the subject of considerable interest for increasing the electrical conductivity of substantially non-conductive matrix materials, the identifying marks described herein are localized within the matrix material and only influence the matrix material's electrical conductivity in proximity to the mark, rather than increasing the bulk conductivity of the matrix material as a whole. That is, because the quantity of electrically conductive carbon nanomaterials used within the identifying marks is small and the mark is localized, the nanomaterial concentration within the matrix material remains below the electrical percolation threshold and does not increase the bulk electrical conductivity of the matrix material on the macroscale.

As an additional level of security, in some embodiments, multiple identifying marks can be present at different locations within the articles described herein. That is, when the article contains more than one identifying mark, each identifying mark is spatially separated in the article from other identifying marks. Spatial separation of multiple marks can also help maintain the carbon nanomaterial below the electrical percolation threshold. Accordingly, in order to produce a counterfeit article, an unauthorized entity would have to locate and accurately reproduce multiple marks, each of which may have different electrical and/or spectroscopic properties or geometric shapes, thereby greatly increasing the effort needed to produce a counterfeit article.

In some embodiments, one or more of the identifying marks can include a different carbon nanomaterial or combination thereof than do the remaining marks. For example, by altering the identity or functionalization of the carbon nanomaterial within an identifying mark, the mark's electrical conductivity can be tailored, thereby changing its electrical signature in a manner that is only readily known by an authorized entity. Hence, an unauthorized entity would have difficulty in properly configuring the composition of an identifying mark in order to replicate its properties in a counterfeit article. In addition, in some embodiments, an identifying mark can contain at least carbon nanotubes having a registered distribution of chiralities. The registered distribution of chiralities can provide another layer of security for preventing replication of the mark by an unauthorized entity. Hence, an identifying mark containing carbon nanotubes with a registered chirality distribution can be authenticated by spectroscopic interrogation, electrical interrogation, or any combination thereof.

In some embodiments, one or more of the identifying marks can include a different amount of carbon nanomaterial or combination thereof per unit area than do the remaining marks. By increasing the amount of carbon nanomaterial per unit area, the electrical conductivity of the mark can be increased. Increasing the amount of carbon nanomaterial per unit area can entail, for example, increasing the thickness of a carbon nanomaterial layer forming the identifying mark. Thus, two identifying marks that otherwise appear to be geometrically identical can produce different electrical responses upon electrical interrogation. Specifically, a mark containing a greater quantity of a carbon nanomaterial in the form of a thicker carbon nanomaterial layer can produce a greater eddy current response during electrical interrogation. An increased amount of carbon nanomaterials can similarly increase the intensity of the spectroscopic response during a spectroscopic interrogation, although the peak positions and ratios remain substantially unchanged.

In some embodiments, each identifying mark can include a plurality of carbon nanotubes having a different registered distribution of chiralities. In other various embodiments, each mark or at least some of the identifying marks can include a plurality of carbon nanotubes having the same registered distribution of chiralities. In either case, in order for an outside entity to reproduce an article containing the identifying marks, the outside entity would need to both locate all the marks and replicate their particular distribution of carbon nanotube chiralities. Similarly, even when an identifying mark does not contain carbon nanotubes having a registered chirality distribution, an outside entity would again need to locate all the marks in an article and replicate the marks' particular geometry and carbon nanomaterial type and amount in order to produce a counterfeit article.

In some embodiments, the identifying marks can be integrated into any layer of the article, and can be used to create marks at various levels for a multilayered architecture that further increases the complexity of the marking process. In some embodiments, the identifying marks can be located within one or more layers of the article, when the article contains one or more layers. When present in multiple layers, the identifying marks can contain the same carbon nanotube chirality distribution in each layer, or different carbon nanotube chirality distributions can be present in at least some of the layers. The patterning of the identifying marks within each layer can also be the same or different. Moreover, in some embodiments, different carbon nanomaterials can be present with the marks within at least some of the layers. For example, in some embodiments, one or more identifying marks containing a plurality of carbon nanotubes having a registered distribution of chiralities can be located in proximity to the exterior of the article. These marks can be spectroscopically or electrically interrogated. In addition, one or more marks can be buried within the interior of the article. These marks need not necessarily contain carbon nanotubes having a registered chirality distribution, although they may, and they can be electrically interrogated, such as through measuring their eddy current signature, as described herein. As discussed above, surface marks can also be electrically interrogated.

In additional embodiments where multiple identifying marks are present within an article, such marks can be formed into a one-dimensional or two-dimensional array of adjacent marks corresponding to two or more identifying spectral signatures. In these embodiments, the security level of the mark can be increased because such configurations further necessitate spatially mapping the spectral output of the mark and correlating both the dimension and spectrum of each segment within the mark. For example, a bar code or other identifying mark can be generated from two or more carbon nanotube sources, each with a registered chirality distribution, where each carbon nanotube source is used to form only a portion of the mark or the two or more carbon nanotube sources are combined within only a portion of the mark. In this case, Raman interrogation can be used to scan across the mark as the spectral signature is captured as a function of position and geometry within the mark. The validation of the mark then represents a function of both the location and width of each spectral signature, as well as the particular spectral features themselves. Other carbon nanomaterials such as graphene can be used in a similar manner.

Figure 5:
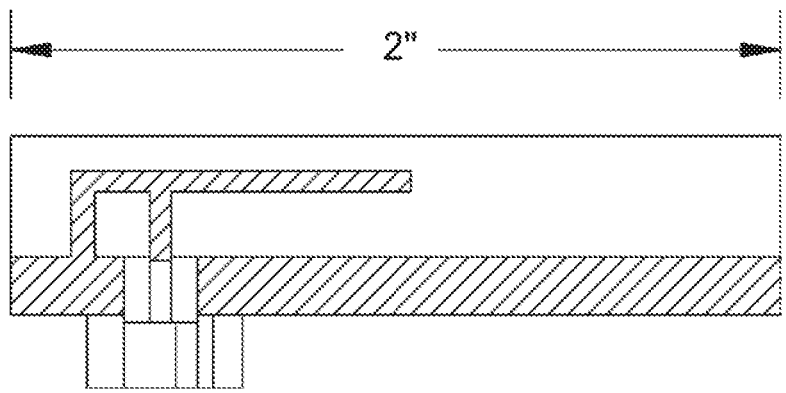
FIG. 5 shows an illustrative schematic of a carbon nanotube antenna structure having an inverted-F antenna configuration.

In still other embodiments, at least a portion of the electrically conductive identifying marks in the article can be configured such that they are in resonant communication with one another. For example, an electrically conductive identifying mark can be configured as an antenna structure within the article, such that the antenna structure is capable of resonant communication with other antenna structures. A carbon nanotube antenna structure, for example, can be fabricated such that it displays a resonant frequency of 2.4 GHz. More generally, the resonant frequency can vary from the kHz range to the GHz range. FIG. 5 shows an illustrative schematic of a carbon nanotube antenna structure having an inverted-F configuration. Besides antennas and resonators, identifying marks containing a carbon nanomaterial can include a metamaterial pattern, in which case the mark is patterned in a 1-D, 2-D or 3-D periodic structural array. In a metamaterial pattern, the array elements provide capacitive and inductive features that produce specific and designed reflectance and transmission characteristics for the array at a designated input frequency.

Figure 6:
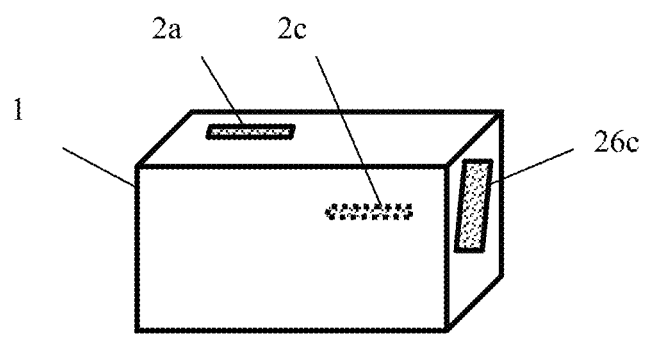
FIG. 6 shows an illustrative schematic of an article marked with a carbon nanomaterial according to the embodiments of the present disclosure.

Accordingly, FIG. 6 shows an illustrative schematic of an article marked with a carbon nanomaterial according to various the embodiments of the present disclosure. As shown in FIG. 6, article 1 contains identifying marks 2*a*, 2*b* and 2*c* therein. The number of marks and their location in FIG. 6 is not considered to be limiting of the present disclosure. The composition of identifying marks 2*a*, 2*b* and 2*c* can contain the same or different carbon nanomaterial or combination thereof. For example, marks 2*a* and 2*c* are on the surface of article 1 and can be electrically interrogated, spectroscopically interrogated, or any combination thereof. When spectroscopically interrogated, marks 2*a* and 2*c*, if desired, can contain at least carbon nanotubes having a registered distribution of chiralities. Mark 2*b*, in contrast, is buried within article 1 and can be assayed through electrical interrogation techniques, such as through measuring the eddy current. In some embodiments, identifying marks 2*a*-2*c* can be in resonant communication with one another. A combination of electrical and spectroscopic identification techniques can be used to locate and authenticate marks 2*a*-2*c* according to the embodiments described herein.

In various embodiments, methods for marking an article with one or more identifying tags containing a carbon nanomaterial and thereafter tracking the article are described herein. In some embodiments, methods described herein can include: providing an article in need of tracking; applying an identifying mark to a surface of the article, the identifying mark not being visible to the naked eye and containing a nanomaterial that includes a plurality of carbon nanotubes having a registered distribution of chiralities; operationally deploying the article; and after operationally deploying the article, optically interrogating the article with electromagnetic radiation to assay the identifying mark. As described above, the registered distribution of chiralities can be known to a manufacturer or a supplier of an article, but not to an end user or other outside entity who may wish to replicate the article, thereby providing improved protection for the manufacturer or supplier against theft and production of counterfeit copies of the article. In addition to or as an alternative of carbon nanotubes, other carbon nanomaterials can be used similarly in this regard, as described herein.

In some embodiments, optically interrogating the article can include obtaining a fluorescence spectrum or a Raman spectrum of the identifying mark. In some embodiments, both a fluorescence spectrum and a Raman spectrum can be obtained to fully characterize the distribution of carbon nanotube chiralities in the identifying mark (i.e., to show the distribution of metallic carbon nanotube chiralities relative to semiconducting carbon nanotube chiralities). In further embodiments, the relative peak intensities of the fluorescence spectrum can be compared to those of the Raman spectrum to verify that overlapping peaks are not present in the Raman spectrum. In some or other embodiments, optically interrogating the article can include obtaining the optical reflectance of the identifying mark, or assaying the non-linear optical properties of the mark.

In some embodiments, methods described herein can include comparing the fluorescence spectrum and/or Raman spectrum produced upon optical interrogation of the identifying mark and comparing the spectrum/spectra to the registered distribution of carbon nanotube chiralities in the plurality of carbon nanotubes originally used to apply the mark. That is, in some embodiments, the methods described herein can include determining a distribution of carbon nanotube chiralities in the identifying mark from the fluorescence spectrum or the Raman spectrum, and comparing the distribution of carbon nanotube chiralities to the registered distribution of chiralities in the plurality of carbon nanotubes used to apply the identifying mark to the article. If the two chirality distributions match within experimental error, as well as the mark's expected physical location and dimensions within the article, the article can be confirmed with some certainty as being authentic. If the two chirality distributions measurably differ, or if the identifying mark otherwise unexpectedly differs in configuration or position, further investigation into the authenticity of the article may be needed. Although unlikely, non-matching chirality distributions need not necessarily indicate the presence of a counterfeit article. For example, environmental conditions (e.g., chemicals, ultraviolet radiation, and the like) can measurably change the spectral fingerprint of an authentic identifying mark over time to a sufficient degree to bring the article's authenticity into question. Various means can be used to protect the carbon nanotubes from unwanted environmental conditions or other factors, as generally discussed above. For example, in some embodiments, a coating can be applied to the article to protect the identifying mark or to provide additional functions. Specifically, in some embodiments, methods described herein can further include applying a coating onto the article that cover at least the identifying mark, where the coating still allows the article to be spectroscopically interrogated.

As discussed above, any population of carbon nanotubes having a registered distribution of chiralities can be used in accordance with the embodiments described herein. In some embodiments, the carbon nanotubes having a registered distribution of chiralities can include those produced from a carbon nanotube synthetic process, optionally following purification of the carbon nanotubes.

In some or other embodiments, the methods described herein can include formulating the plurality of carbon nanotubes to have a non-native distribution of carbon nanotube chiralities. Formulating the plurality of carbon nanotubes to have a non-native distribution of carbon nanotube chiralities can be accomplished in several different manners, as described in more detail above. In still other embodiments, at least a portion of the carbon nanotubes can be functionalized, as also described above.

In various embodiments, applying an identifying mark to an article can further include preparing or obtaining a solution or suspension of carbon nanotubes having a registered distribution of carbon nanotube chiralities. In general, any solvent that provides good dispersion or solubilization of the carbon nanotubes can be used in accordance with the present embodiments. Various surfactants can also be used in conjunction with the solvent in this regard. In more particular embodiments, the solvent used in conjunction with applying the identifying mark to the article can represent a volatile solvent, which can aid in its removal from the article by evaporation following application of the mark. Applying the solution or suspension of carbon nanotubes to the article can take place by any suitable technique. In various embodiments, application of the carbon nanotubes to the article to produce the identifying mark can take place by spray coating, spin coating, printing, or any combination thereof. In some embodiments, these techniques can be used to produce substantially a monolayer of carbon nanotubes on the surface of the article.

In related embodiments, identifying marks configured for electrical interrogation of the mark can be used in authenticating an operationally deployed article. In some embodiments, the electrical interrogation techniques can be used in concert with or as an alternative to spectroscopic interrogation techniques.

In some embodiments, methods described herein can include incorporating an identifying mark on or within an article in need of tracking; operationally deploying the article; and after operationally deploying the article, electrically interrogating the article to assay the identifying mark. The identifying mark employed in such methods is localized, electrically conductive, contains a carbon nanomaterial and is not visible to the naked eye.

Although any technique for electrically interrogating the article and its identifying marks can be used within the context of the present disclosure, particularly suitable techniques can include measuring eddy currents within the article. Accordingly, in some embodiments, electrically interrogating the article can include scanning the article with an eddy current probe.

The theory underlying eddy current probes and suitable eddy current probes for practicing the embodiments described herein will be understood by one having ordinary skill in the art. Accordingly, a detailed discussion of such will not be provided herein. In brief, an eddy current probe produces an alternating current at the end of the probe. The alternating current, in turn, produces an alternating magnetic field in the same location. By placing an eddy current probe in proximity to a conductive material, such as the electrically conductive identifying marks described herein, the alternating magnetic field produces an electric current in the conductive material through an inductance process. The induced electrical currents are referred to as eddy currents. In turn, the eddy currents produce an opposing magnetic field that resists the magnetic field being generated by the eddy current probe. The magnetic field interaction is dependent upon the distance between the eddy current probe and the conductive material, and a voltage output of the probe can be correlated to the distance between the probe and the conductive material. By spatially mapping an article with an eddy current probe, areas of the article demonstrating increased eddy current activity can be determined as containing an identifying mark of the present disclosure.

Since the conductive material need not necessarily be on the article's surface in order to measure the eddy current activity, eddy current probes can be used to electrically interrogate an article having an identifying mark on and/or within a portion of the article. More specifically, eddy current measurements can be used to electrically interrogate an article having an identifying mark located on or within a portion of a substantially non-conductive matrix material forming the article.

As discussed above, suitable carbon nanomaterials for inclusion in identifying marks to be electrically interrogated can include carbon nanotubes, graphene, any functionalized variant thereof (e.g., functionalized carbon nanotubes or functionalized graphene), or any combination thereof. In some embodiments, the carbon nanomaterial forming the identifying mark can include at least carbon nanotubes, and the carbon nanotubes can have a registered distribution of chiralities.

In further embodiments, methods described herein can also include both electrically and spectroscopically interrogating an article in order to locate and authenticate one or more identifying marks therein. Spectroscopic interrogation techniques can be employed with identifying marks that include a plurality of carbon nanotubes containing a registered distribution of chiralities. Accordingly, in some embodiments, methods described herein can further include obtaining a fluorescence spectrum or a Raman spectrum of the identifying mark, determining a distribution of carbon nanotube chiralities in the identifying mark from the fluorescence spectrum or the Raman spectrum, comparing the distribution of carbon nanotube chiralities to the registered distribution of chiralities, and authenticating the identifying mark based on its electrical properties and the distribution of carbon nanotube chiralities.

Although the invention has been described with reference to the disclosed embodiments, those skilled in the art will readily appreciate that these only illustrative of the invention. It should be understood that various modifications can be made without departing from the spirit of the invention. The invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

What is claimed is the following:

1. An article comprising:
    a matrix; and
    a subsurface identifying mark that is configured for indirect electrical interrogation, is localized within the matrix and is not visible to a naked eye, the subsurface identifying mark being electrically conductive and comprising a carbon nanomaterial.

2. The article of claim 1, wherein the matrix comprises a non-conductive matrix material, and the identifying mark does not increase a bulk conductivity of the non-conductive matrix material.

3. The article of claim 1, wherein the carbon nanomaterial comprises carbon nanotubes, graphene, any functionalized variant thereof, or any combination thereof.

4. The article of claim 3, wherein the carbon nanomaterial comprises at least carbon nanotubes, and the carbon nanotubes have a registered distribution of chiralities.

5. The article of claim 3, wherein the article comprises more than one subsurface identifying mark, each subsurface identifying mark being spatially separated in the article.

6. The article of claim 5, wherein one or more of the subsurface identifying marks comprise a different carbon nanomaterial or combination thereof than do the remaining subsurface identifying marks.

7. The article of claim 5, wherein one or more of the subsurface identifying marks comprise a different amount of carbon nanomaterial or combination thereof per unit area than do the remaining subsurface identifying marks.

8. The article of claim 1, wherein the article is an electrical device comprising an electronic component.

9. The article of claim 8, wherein the subsurface identifying mark is in electrical communication with the electronic component.

10. An article comprising:
    more than one identifying mark comprising a carbon nanomaterial, each identifying mark being localized and spatially separated in the article, not visible to a naked eye, and electrically conductive;
    wherein at least a portion of the identifying marks are in resonant communication with one another.

11. A method comprising:
    providing an article in need of tracking, the article comprising a matrix and a subsurface identifying mark incorporated within the article, the subsurface identifying mark being localized within the matrix, electrically conductive, and not visible to a naked eye, and comprising a carbon nanomaterial;
    operationally deploying the article; and
    after operationally deploying the article, electrically interrogating the article to locate and assay the subsurface identifying mark.

12. The method of claim 11, wherein electrically interrogating the article comprises scanning the article with an eddy current probe.

13. The method of claim 11, wherein the matrix comprises a non-conductive matrix material, and the identifying mark does not increase a bulk conductivity of the non-conductive matrix material.

14. The method of claim 11, wherein the carbon nanomaterial comprises carbon nanotubes, graphene, any functionalized variant thereof, or any combination thereof.

15. The method of claim 14, wherein the carbon nanomaterial comprises at least carbon nanotubes, and the carbon nanotubes have a registered distribution of chiralities.

16. The method of claim 14, wherein the article comprises more than one subsurface identifying mark, each subsurface identifying mark being spatially separated in the article.

17. The method of claim 16, wherein at least a portion of the subsurface identifying marks are in resonant communication with one another.

18. The method of claim 16, wherein one or more of the subsurface identifying marks comprise a different carbon nanomaterial or combination thereof than do the remaining subsurface identifying marks.

19. The method of claim 16, wherein one or more of the subsurface identifying marks comprise a different amount of carbon nanomaterial or combination thereof per unit area than do the remaining subsurface identifying marks.

20. A method comprising:
    providing an article in need of tracking, the article comprising an identifying mark, the identifying mark being localized, electrically conductive, and not visible to a naked eye, and comprising a carbon nanomaterial;
  wherein the carbon nanomaterial comprises at least carbon nanotubes having a registered distribution of chiralities;

operationally deploying the article;

after operationally deploying the article, electrically interrogating the article to locate and assay the identifying mark;

obtaining a fluorescence spectrum or a Raman spectrum of the identifying mark;

determining a distribution of carbon nanotube chiralities in the identifying mark from the fluorescence spectrum or the Raman spectrum;

comparing the distribution of carbon nanotube chiralities to the registered distribution of chiralities; and authenticating the identifying mark based on its electrical properties and the distribution of carbon nanotube chiralities.

* * * * *